United States Patent
Patel (10) Patent No.: US 7,137,534 B2
(45) Date of Patent: Nov. 21, 2006

(54) CLEANSING AGENT AND AIR FRESHENER DISPENSER

(76) Inventor: Abdul Ebrahim Patel, 189 Plashet Grove Eastham, London (GB) E8 1BX (*) Notice: Subject to any disclaimer, the term of this patent is extended or adjusted under 35 U.S.C. 154(b) by 67 days.

(21) Appl. No.: 10/427,331

(22) Filed: May 1, 2003

(65) Prior Publication Data
US 2004/0108338 A1 Jun. 10, 2004

Related U.S. Application Data

(63) Continuation-in-part of application No. 10/415,131, filed as application No. PCT/GB01/04614 on Oct. 16, 2001, now abandoned.

(30) Foreign Application Priority Data
Oct. 26, 2000 (GB) .............................. 98 0026229.5

(51) Int. Cl.
*B67D 1/07* (2006.01)
*G01F 11/00* (2006.01)
(52) U.S. Cl. .................. 222/192; 222/129; 222/252; 222/320; 222/402.1; 222/135; 222/321.7
(58) Field of Classification Search ................ 222/129, 222/134, 135, 144.5, 173, 181.1, 181.2, 181.3, 222/187, 192, 252, 320–321.9, 325, 402.1, 222/255; 239/40–43, 60, 289
See application file for complete search history.

(56) References Cited
U.S. PATENT DOCUMENTS

| | | | |
|---|---|---|---|
| 4,084,732 A | 4/1978 | Dearling | |
| 4,711,375 A | 12/1987 | Mader et al. | |
| 5,165,603 A * | 11/1992 | Hahn | 239/55 |
| 5,367,716 A * | 11/1994 | Huang | 4/222 |
| 5,379,917 A | 1/1995 | Brown et al. | |
| 5,595,324 A | 1/1997 | Brown et al. | |
| 5,799,826 A | 9/1998 | Brown et al. | |
| 6,032,819 A * | 3/2000 | Hanna | 220/501 |
| 6,062,425 A | 5/2000 | Brown et al. | |
| 6,610,254 B1 * | 8/2003 | Furner et al. | 422/123 |
| 6,769,631 B1 * | 8/2004 | Brown | 239/289 |
| 2002/0030116 A1 * | 3/2002 | Brown | 239/59 |

FOREIGN PATENT DOCUMENTS

EP 8830998.9 4/1989

* cited by examiner

*Primary Examiner*—Patrick Brinson
(74) *Attorney, Agent, or Firm*—Miller Nash, LLP (57) ABSTRACT

A liquid soap container comprising of a dispensing pump which incorporates a pressurised air freshener canister or a liquid air freshener container. When a dispensing pump is depressed it also activates the valve of a pressurised air freshener canister or a pump for a liquid air freshener container to refresh the air whilst at the same time dispensing the liquid or gel soap. After the action of depressing the pump has stopped the release of the air freshener also stops. Both systems work simultaneously. An air vent casing helps secure the air freshener canister or the liquid air freshener container, and also temporarily contains the released air freshener before it vaporises or evaporates in to the atmosphere.

37 Claims, 8 Drawing Sheets

CLEANSING AGENT AND AIR FRESHENER DISPENSER

This application is a continuation-in-part application of prior application Ser. No. 10/415,131, filed Apr. 25, 2003 now abandoned, which is the National Stage of International Application No. PCT/GB01/04614, filed Oct. 16, 2001, which was an International Application based on United Kingdom Patent Application No. 0026229.5, filed Oct. 26, 2000.

BACKGROUND OF THE INVENTION

This invention relates to a cleansing agent and an air freshener dispenser.

Liquid soaps and air fresheners on their own are well known. A liquid soap comprises of a container usually made of HDPE, PVC, or PET. The container has a dispensing pump which is screwed on to the neck of the container which when depressed dispenses the liquid soap in the container.

An air freshener comes in many forms and designs but technically all perform the same task i.e. to make a confined space e.g. a toilet, bathroom, kitchen etc. smell more pleasantly by neutralising an offensive odour and replacing it with a pleasant smell. Air fresheners come in a solid gel, liquid, or pressurised gas canister.

These two systems of washing hands and deodorising a room at this moment in time is relatively expensive as a consumer has to purchase both separately. Moreover the use of an air freshener in the gas canister or a liquid form become active only when a person physically takes the canister in his hand and sprays the room. In the liquid air freshener system a person has to pour the liquid perfume on to a sponge or pot pourri.

Both of these acts are by human nature forgetful especially in a bathroom, toilet, kitchen, commercial or public environment. A person is almost certain to wash his hands after using the toilet or after cooking in a kitchen and it is this habit that is being utilised to create the invention.

SUMMARY OF THE INVENTION

The object of this invention is to provide a product which combines both features in one by using our human habit of washing hands to activate an air freshener with the use of dispensing means. This system provides advantages in cost and effective use of an air freshener as this invention automatically dispenses a cleansing agent such as liquid soap but also activates an air freshener. This invention also fills a gap in the market as at present both products have to be purchased separately. This invention is of particular use in a toilet situation where washing hands with an antibacterial soap and deodorising the toilet can be achieved in one simple step.

The volume of dispensation of the cleansing agent may correspond to the volume of dispensation of the air freshener so that when the cleansing agent has emptied out so too has the air freshener.

Where reference is being made to liquid soap, this also includes soaps that are essentially liquid but for thickeners and/or gelling agents that are incorporated in the soap formulation to make the soap a gel or semi liquid/gel soap.

Further, though reference is being made to gas and liquid air fresheners in this description, a useful feature in this concept is the incorporation of a slow-release solid, gel or liquid air freshener as well within the apparatus described herein. This method allows a complete product in that the solid, gel or liquid air freshener will slowly release fragrance, giving continuous fragrance action whilst the gas or liquid air freshener will give a burst of air freshener when soap is dispensed.

Yet another feature within the scope of this invention is a method to disengage, disconnect, or remove the dispensation of air freshener when the dispensation of soap is activated. This feature is helpful in that it gives a user a choice whether or not to activate the dispensation of air freshener when the soap dispensing means are activated. This avoids wastage of air freshener when a user might feel he does not need it. A further advantage of this feature is that it makes the apparatus in the invention more marketable.

The uses of this product will not only be limited to domestic households but would be of effective use in commercial and public premises e.g. office buildings, public toilets, hotels etc. As well as potential uses in all modes of transport e.g. Aeroplanes, trains, ships etc.

Preferred embodiments of the invention will now be described, by way of example using a domestic type of dispensing pump though the concept as it applies to a commercial type dispensing pump is the same.

BRIEF DESCRIPTION OF THE DRAWINGS

FIG. 9. In this method the supply of soap 31 is filled in its container 32, the supply of soap is dispensed by means of dispensing pump 33 by manually pushing its dispensing handle 34. This action puts pressure on the air freshener container 35 by means of disc 36. This in turn will activate the air freshener valve 37 which dispenses the air freshener 39. The released air freshener will now escape through rented holes 32. Any excess air freshener that does not escape will be absorbed by an absorbent material 41.

FIG. 10. Shows the concept being applied to different shape of container 42. Here the diagram, shows the invention in action. Soap 43 is dispensed by depressing the pump which in turn releases air freshener 44 from its valve 45. The air freshener container 46 sits within the vented casing 47. Any excess vapour is absorbed by absorbent material 48.

FIG. 11. Shows the invention does not necessarily use a lever to activate the air freshener. Here the action of depressing the pump 49 causes the dispensation of soap 50 contained in its container 51. The action of depressing the pump will put pressure on the valve of the air freshener container 52, there by releasing air freshener within its vented casing 53.

FIG. 15. Shows the apparatus in a liquid air freshener system. Here the liquid air freshener container has a pump 57 which when activated releases a spray of liquid air freshener. Once again the means of activation is through the use of a soap dispensing pump that operates the air freshener pump. Once again in this apparatus the slow-release air freshener 56 is combined in the apparatus to provide continuous fragrancing.

DESCRIPTION OF THE PREFERRED EMBODIMENT

Gas Canister System

Figure 1:
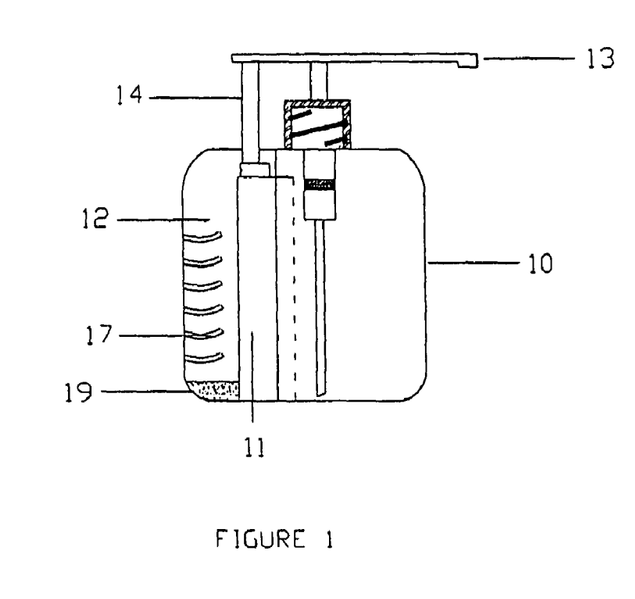
FIG. 1. Shows the side view of the liquid soap container with its dispensing pump and the pressurised canister of air freshener incorporated along the side wall of the liquid soap container and air vent casing.

Referring to the drawing in FIG. 1 the liquid soap container 10, has been specially designed to accommodate the air freshener canister 11, which sits along side the air vent casing 12. The dispensing pump 13 has a lever 14 that activates the valve of the gas air freshener canister 11. The valve may be a metered valve.

Figure 2:
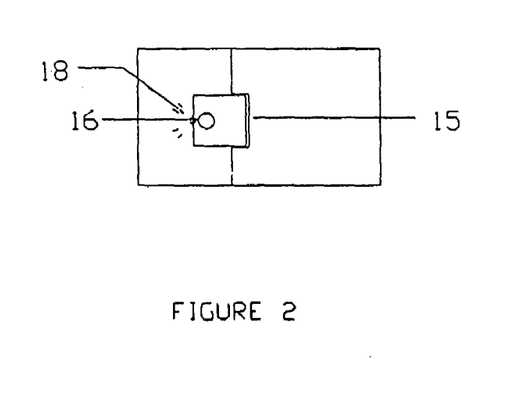
FIG. 2. Shows the horizontal plain view of the liquid soap container to demonstrate how the pressurised canister is incorporated within the liquid soap container and the air vent casing.

Referring to the drawing in FIG. 2 the gas air freshener is held laterally within the liquid soap container by a vertical notch 15.

Figure 3:
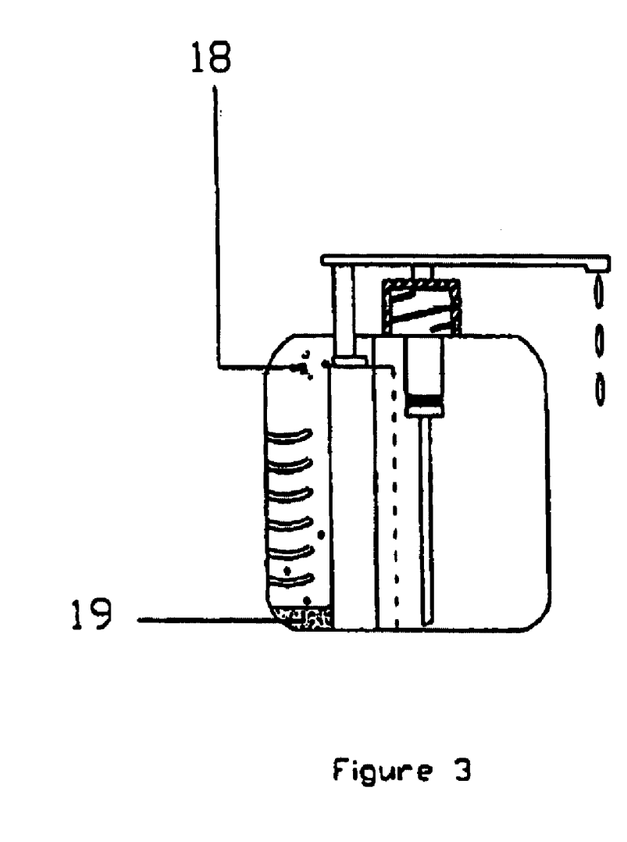
FIG. 3. Illustrates the invention in action with the dispensing pump being in a depressed position that allows the liquid soap to be dispensed from the pump. At the same time the lever is adapted so that the dispensing pump activates the pressurised canister valve releasing the air freshener within the air vent casing.

Referring to FIG. 3 the lever 14 has now depressed the gas canister which activates is valve and sprays from its pin hole 16 within the air vent casing that is fully formed i.e. without air vents at that position to prevent spraying on to the walls or directly into the atmosphere. Below the position of the spray pin hole 16 are air vents 17 for the air freshener vapour 18 to escape through into the atmosphere.

At the bottom of the gas canister is an absorbent material 19 which absorbs any further vapour that has not escaped through the air vents 17.

Figure 4:
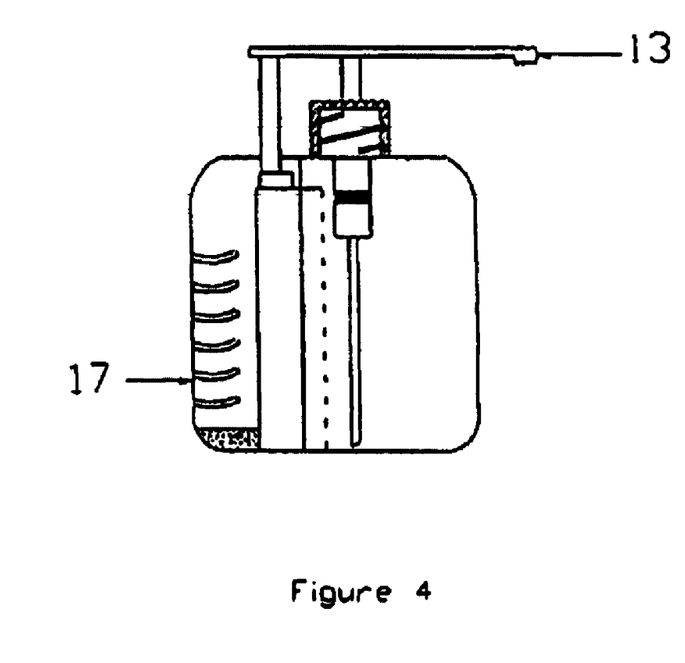
FIG. 4. Illustrates that once the dispensing pump is no longer depressed the air freshener canister too is no longer activated. Both systems work simultaneously.

Referring to the drawing in FIG. 4 once the dispensing pump 13 is no longer depressed a spring within the dispensing pump pushes it upwards and thereby simultaneously deactivates the valve of the gas canister. The system is now ready for a second application.

Liquid Air Freshener System

Figures 5, 6:
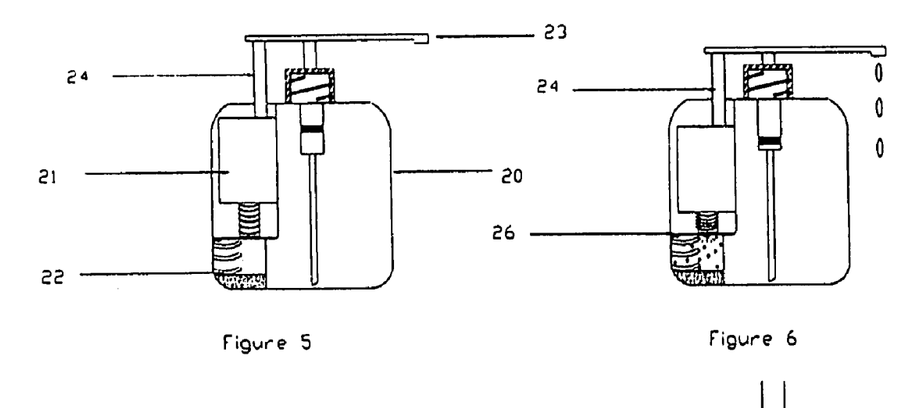
FIG. 5. Illustrates the same example as in FIG. 1 except that this is adapted to a liquid air freshener system.
FIG. 6. Illustrates the same as FIG. 3 except that it shows the liquid air freshener being dispensed and subsequently absorbed by a sponge that helps to evaporate the air freshener.
Figure 7:
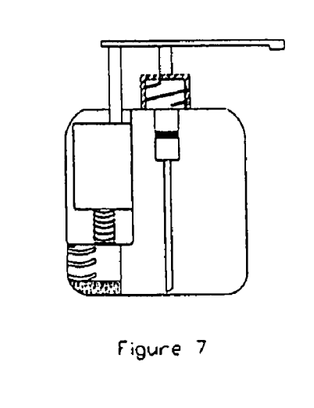
FIG. 7. Illustrates the same as FIG. 4 as it applies to a liquid air freshener container system.

Referring to the drawing in FIG. 5 the liquid soap container 20 has been especially designed to accommodate the liquid air freshener container 21 which sits snugly in between the liquid soap container 20 and the air vent casing 22. The dispensing pump 23 has a lever 24 that when depressed activates a pump of the liquid air freshener container 21 operative to dispense a spray of liquid air freshener.

Figure 8:
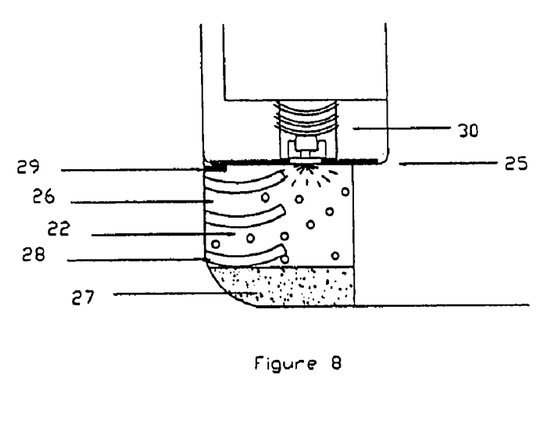
FIG. 8. Shows a detailed view of the mechanisms involved in activating the liquid air freshener system.
Figure 9:
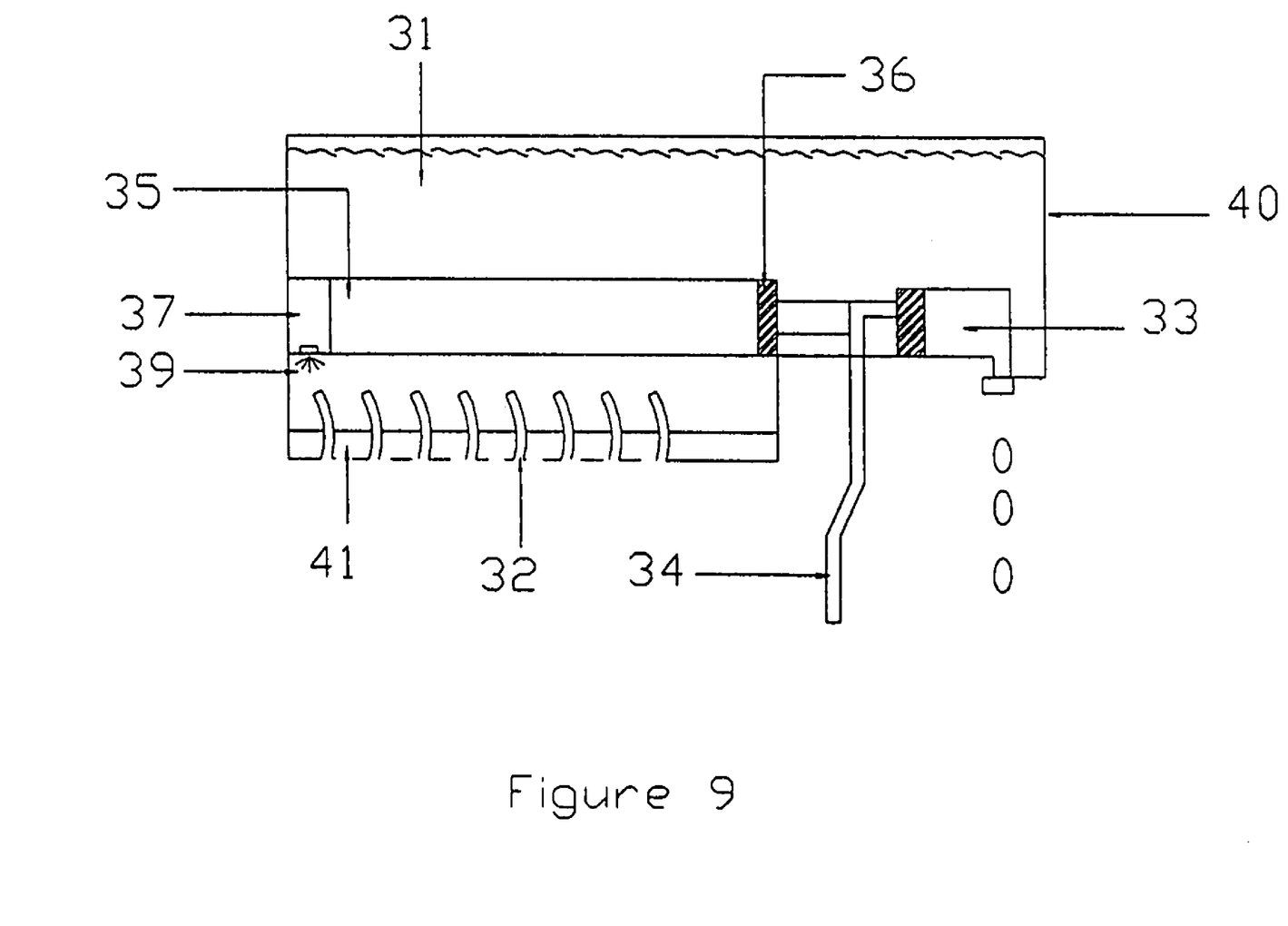
Figure 10:
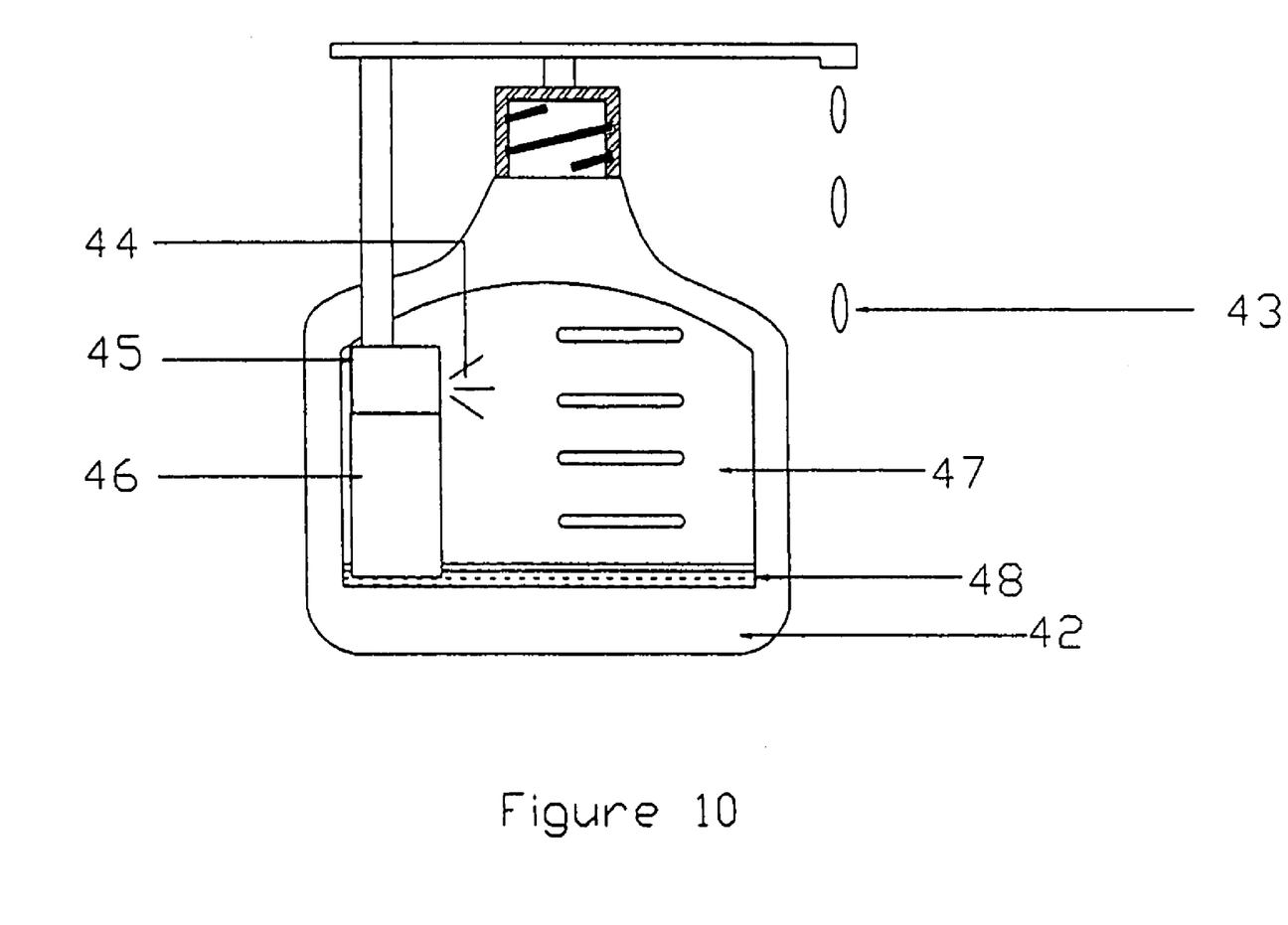
Figure 11:
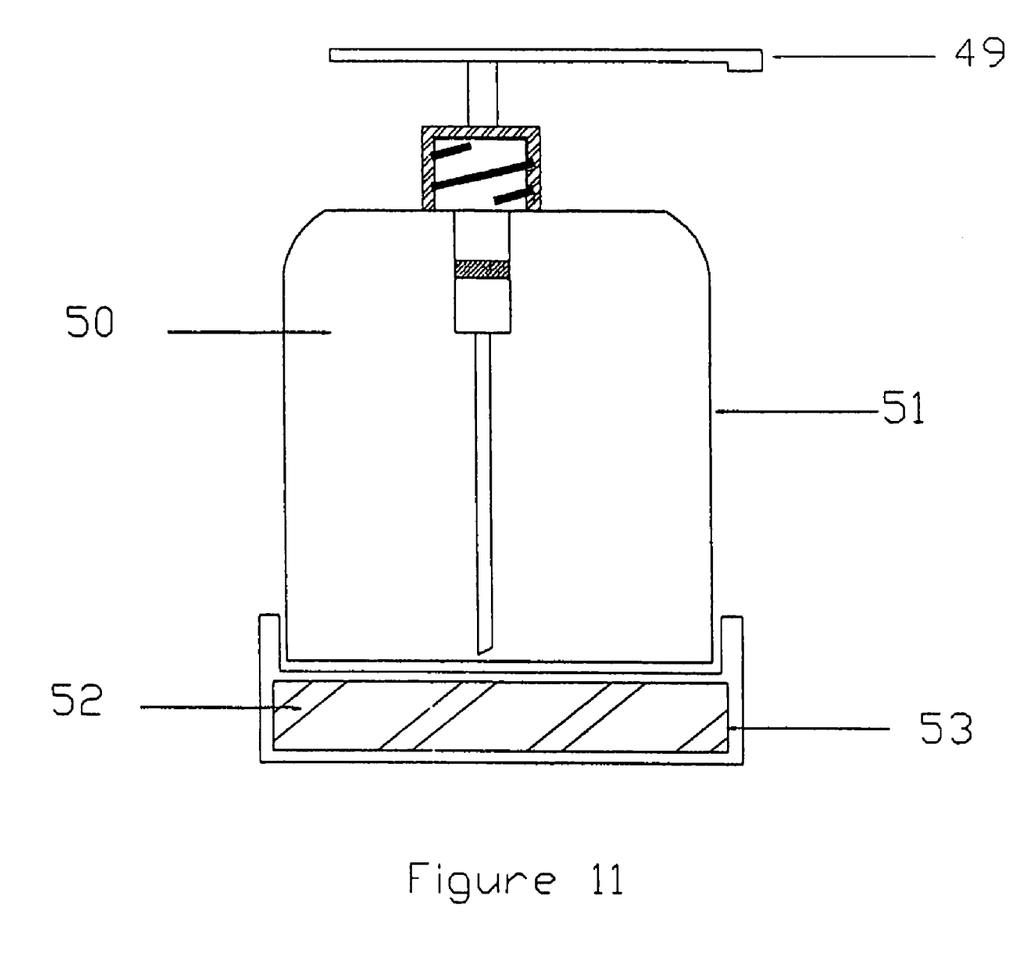
Figure 12:
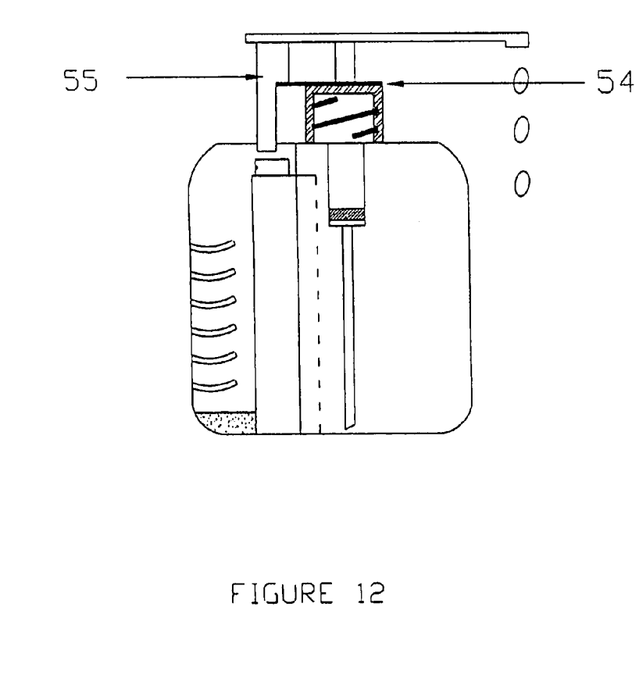
FIG. 12. Shows a method that enables the disconnection of the supply of air freshener when the supply of soap is activated. Here an additional stopper 54 is placed within the lever. When the disc 55 is aligned to face the lever, the air freshener is disconnected as depressing the soap pump will not allow the lever to travel further down to press directly or indirectly against the valve of the air freshener. Soap will be dispensed without the air freshener.
Figure 13:
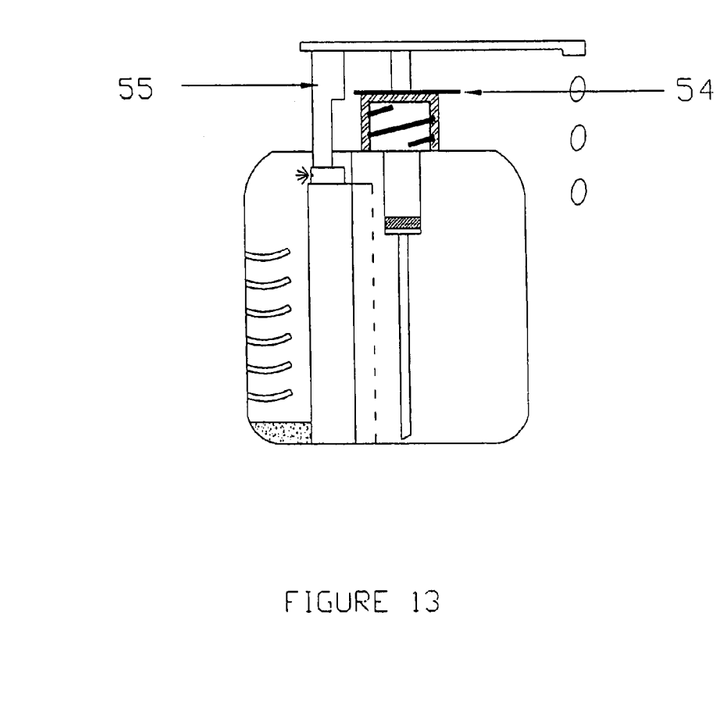
FIG. 13. Shows if the disc is rotated away from the lever this will now allow the lever to travel fully to press directly or indirectly against the valve of the air freshener thereby activating the dispensation of the air freshener.
Figure 14:
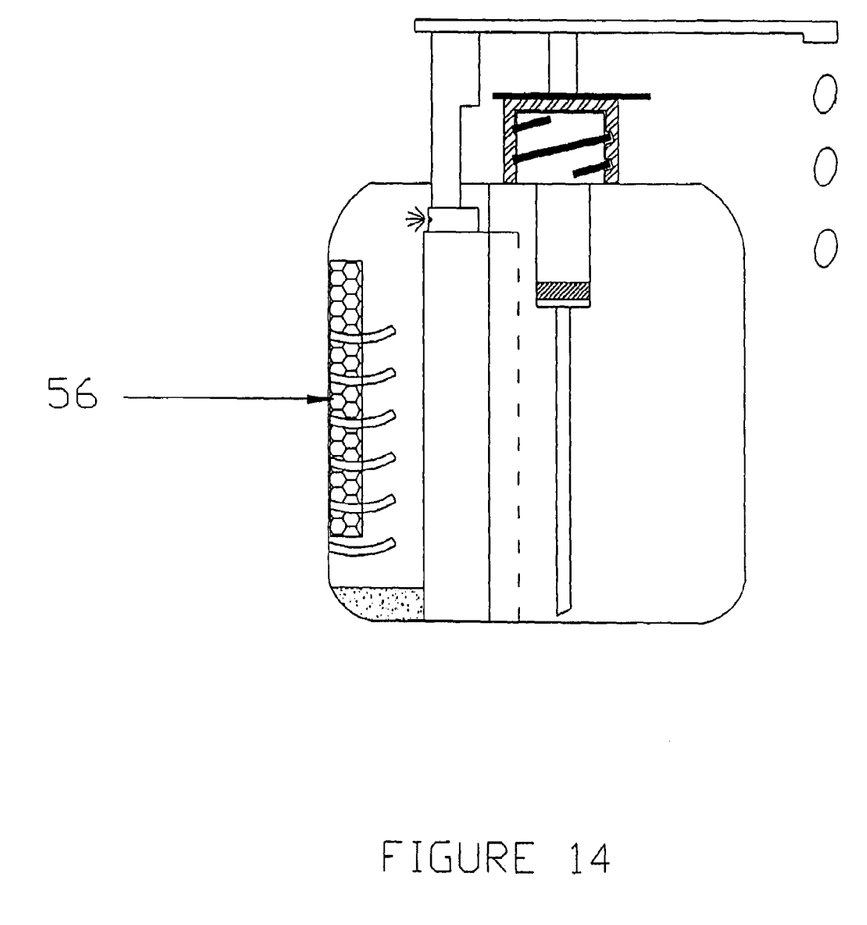
FIG. 14. Shows the incorporation of a solid, gel or liquid air freshener 56 with a gas canister air freshener so that the two systems of air freshener complement each other. The solid, gel or liquid air freshener will have continues fragrance action whilst the gas or liquid air freshener will give a burst of air freshener the dispensing pump for soap is activated.

Referring to the drawing in FIGS. 6 and 8 the liquid air freshener container 21 slides up and down vertically up to a notch 25 on the liquid soap container 20 and a corresponding notch 26 on the air vent casing 22. The soap dispensing pump 23 when depressed also pushes an adapted lever 24 vertically downwards which then activates the liquid air freshener pump to spray directly on to the sponge 27. The liquid air freshener droplets now on the sponge evaporates through the air vents 28.

Referring to the drawing in FIG. 8 the liquid air freshener is dispensed by means of the notches 25 and 26 pressing on to a releasing ring 29 via a spring 30 that activates the air freshener pump to spray air freshener on to an absorbent material. The spring 30 is located at the neck of the liquid air freshener container 21 and sits between the notches 25 and 26 and the shoulder of the liquid air freshener container. The function of the releasing ring 29 is to activate the pump of the liquid air freshener container as it is pressed downwards on to the notches 25 and 26.

The function of the spring 30 is to bring back the liquid air freshener container to its normal resting position and thereby release the pump. This mechanism will work simultaneously with the up and down movement of the dispensing pump.

Additionally, FIG. 15. shows the apparatus in a liquid air freshener system. Here the liquid air freshener container has a pump 57 which when activated releases a spray of liquid air freshener. Once again the means of activation is through the use of a soap dispensing pump that operates the air freshener pump. Once again in this apparatus the slow release air freshener 56 is combined in the apparatus to provide continuous fragrancing.

Any means of dispensing a cleaning agent and air freshener simultaneously through the same or separate apertures will embody the invention. For example the cleansing agent may be dispensed through a pump and the air freshener through a valve, or vice versa.

Both the cleansing agent and the air freshener may be dispensed through pumps. Both the cleaning agent and the air freshener may take any suitable form.

The invention claimed is:

1. Apparatus comprising a container for cleansing agent, a user operable means for dispensing cleansing agent from the container therefor, and a pressurized container of air freshener comprising a user operable valve for dispensing air freshener from the container therefor, the apparatus being arranged such that operation of the means for dispensing cleansing agent causes operation of the valve to dispense air freshener.

2. Apparatus as claimed in claim 1 further comprising a vented casing into which air freshener is dispensed from the container for air freshener, and from which dispensed air freshener can escape into the atmosphere.

3. Apparatus as claimed in claim 1 further comprising a vented casing into which air freshener is dispensed from the container for air freshener, and from which released air freshener can escape into the atmosphere wherein the container for air freshener is accommodated within the casing.

4. Apparatus as claimed in claim 1 further comprising a vented casing into which air freshener is dispensed from the container for air freshener, and from which dispensed air freshener can escape into the atmosphere wherein the container for air freshener is accommodated within the casing and slidably mounted relative to the casing and/or container for cleansing agent.

5. Apparatus as claimed in claim 1 further comprising a vented casing into which air freshener is dispensed from the container for air freshener, and from which dispensed air fresher can escape into the atmosphere wherein the container for air freshener is accommodated within the casing and slidably mounted relative to the casing and/or container for cleansing agent, and the container for cleansing agent comprises notches to arrest sliding movement of the container for air freshener.

6. Apparatus as claimed in claim 1 further comprising a vented casing into which air freshener is dispensed from the container for air freshener, and from which dispensed air freshener can escape into the atmosphere wherein the casing is arranged to prevent spraying of air freshener directly into the atmosphere.

7. Apparatus as claimed in claim 1 comprising a material to absorb excess air freshener.

8. Apparatus as claimed in claim 1 further comprising a vented casing into which air freshener is dispensed from the container for air freshener, and from which dispensed air freshener can escape into the atmosphere and a material to absorb air freshener, wherein the material sits in a cavity between the container for cleansing agent and the casing.

9. Apparatus as claimed in claim 1, wherein the container for air freshener is a pressurised gas canister.

10. Apparatus as claimed in claim 1, wherein the container for air freshener is a liquid air freshener container.

11. Apparatus as claimed in claim 1, wherein the container for cleansing agent is a liquid soap or gel soap container.

12. Apparatus as claimed in claim 1 comprising a release ring operative to operate the valve when the means for dispensing cleansing agent are operated.

13. Apparatus as claimed in claim 1, wherein the size of the containers for cleansing agent and for air freshener and the volume of cleansing agent and air freshener dispensed when the means for dispensing cleansing agent are operated are selected so that when the container for cleansing agent has emptied so too has the container for air freshener.

14. Apparatus as claimed in claim 1, wherein the means for dispensing cleansing agent comprises a lever operative to operate the means for dispensing air freshener.

15. Apparatus as claimed in claim 1, wherein the container for air freshener is accommodated within or adjacent to the container for cleansing agent.

16. Apparatus as claimed in claim 1 comprising an arrangement to allow a user to selectively prevent the dispensation of air freshener when the means for dispensing cleansing agents are activated.

17. Apparatus as claimed in claim 1 comprising a slow-release solid, gel or liquid air freshener and a gas and/or liquid air freshener.

18. Apparatus as claimed in claim 1 wherein the means for dispensing cleansing agent comprises a pump.

19. Apparatus as claimed in claim 1 wherein the means for dispensing cleansing agent comprises a valve.

20. Apparatus as claimed in claim 1 comprising one or more springs to close the valve of the air freshener container.

21. Apparatus comprising a container for cleansing agent, a means for dispensing cleansing agent from the container therefor, and a container for air freshener comprising a pump for dispensing a spray of air freshener from the container therefor, the apparatus being arranged such that operation of the means for dispensing cleansing agent causes operation of the pump to dispense a spray of air freshener, said apparatus further comprising a material to absorb excess air freshener.

22. Apparatus as claimed in claim 21 further comprising a vented casing into which air freshener is dispensed from the container for air freshener, and from which dispensed air freshener can escape into the atmosphere.

23. Apparatus as claimed in claim 21 further comprising a vented casing into which air freshener is dispensed from the container for air freshener, and from which released air freshener can escape into the atmosphere wherein the container for air freshener is accommodated within the casing.

24. Apparatus comprising a container for cleansing agent, a means for dispensing cleansing agent from the container therefor, and a container for air freshener comprising a pump for dispensing a spray of air freshener from the container therefor, the apparatus being arranged such that operation of the means for dispensing cleansing agent causes operation of the pump to dispense a spray of air freshener, further comprising a vented casing into which air freshener is dispensed from the container for air freshener, and from which dispensed air freshener can escape into the atmosphere wherein the container for air freshener is accommodated within the casing and slidably mounted relative to the casing and/or container for cleansing agent.

25. Apparatus comprising a container for cleansing agent, a means for dispensing cleansing agent from the container therefor, and a container for air freshener comprising a pump for dispensing a spray of air freshener from the container therefor, the apparatus being arranged such that operation of the means for dispensing cleansing agent causes operation of the pump to dispense a spray of air freshener, further comprising a vented casing into which air freshener is dispensed from the container for air freshener, and from which dispensed air freshener can escape into the atmosphere wherein the container for air freshener is accommodated within the casing and slidably mounted relative to the casing and/or container for cleansing agent, and the container for cleansing agent comprises notches to arrest sliding movement of the container for air freshener.

26. Apparatus as claimed in claim 21 further comprising a vented casing into which air freshener is dispensed from the container for air freshener, and from which dispensed air freshener can escape into the atmosphere wherein the casing is arranged to prevent spraying of air freshener directly into the atmosphere.

27. Apparatus comprising a container for cleansing agent, a means for dispensing cleansing agent from the container therefor, and a container for air freshener comprising a pump for dispensing a spray of air freshener from the container therefor, the apparatus being arranged such that operation of the means for dispensing cleansing agent causes operation of the pump to dispense a spray of air freshener, further comprising a vented casing into which air freshener is dispensed from the container for air freshener, and from which dispensed air freshener can escape into the atmosphere and a material to absorb air freshener, wherein the absorbent material sits in a cavity between the container for cleansing agent and the casing.

28. Apparatus as claimed in claim 21 wherein the container for air freshener is a liquid air freshener container.

29. Apparatus as claimed in claim 21, wherein the container for cleansing agent is a liquid soap or gel soap container.

30. Apparatus comprising a container for cleansing agent, a means for dispensing cleansing agent from the container therefor, a container for air freshener comprising a pump for dispensing a spray of air freshener from the container therefor, and a release ring operative to operate the pump when the means for dispensing cleansing agent are operated, the apparatus being arranged such that operation of the means for dispensing cleansing agent causes operation of the pump to dispense a spray of air freshener.

31. Apparatus as claimed in claim 21, wherein the size of the containers for cleansing agent and for air freshener and the volume of cleansing agent and air freshener dispensed when the means for dispensing cleansing agent are operated are selected so that when the container for cleansing agent has emptied so too has the container for air freshener.

32. Apparatus as claimed in claim 21, wherein the means for dispensing cleansing agent comprises a lever operative to operate the means for dispensing air freshener.

33. Apparatus as claimed in claim 21, wherein the container for air freshener is accommodated within or adjacent to the container for cleansing agent.

34. Apparatus comprising a container for cleansing agent, a means for dispensing cleansing agent from the container therefor, and a container for air freshener comprising a pump for dispensing a spray of air freshener from the container therefor, the apparatus being arranged such that operation of the means for dispensing cleansing agent causes operation of the pump to dispense a spray of air freshener, further comprising an arrangement to allow a user to selectively prevent the dispensation of air freshener when the means for dispensing cleansing agents are activated.

35. Apparatus as claimed in claim 21 comprising a slow-release solid, gel or liquid air freshener and a gas and/or liquid air freshener.

36. Apparatus comprising a container for cleansing agent, a means for dispensing cleansing agent from the container therefor, and a container for air freshener comprising a pump for dispensing air freshener from the container therefore and one or more springs to close a valve of the air freshener container, the apparatus being arranged such that operation of the means for dispensing cleansing agent causes operation of the pump to dispense air freshener, and wherein the means for dispensing cleansing agent comprises a pump.

37. Apparatus as claimed in claim 21 wherein the means for dispensing cleansing agent comprises a valve.

* * * * *